(12) United States Patent
Harada

(10) Patent No.: US 12,251,080 B2
(45) Date of Patent: Mar. 18, 2025

(54) ENDOSCOPE WITH REMOVABLE CAP

(71) Applicant: FUJIFILM Corporation, Tokyo (JP)

(72) Inventor: Takashi Harada, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 517 days.

(21) Appl. No.: 17/675,133

(22) Filed: Feb. 18, 2022

(65) Prior Publication Data

US 2022/0167835 A1    Jun. 2, 2022

Related U.S. Application Data

(63) Continuation of application No. PCT/JP2020/030874, filed on Aug. 14, 2020.

(30) Foreign Application Priority Data

Aug. 22, 2019 (JP) .................................. 2019-151976

(51) Int. Cl.
    *A61B 1/00* (2006.01)
    *A61B 1/018* (2006.01)

(52) U.S. Cl.
    CPC ...... *A61B 1/00137* (2013.01); *A61B 1/00098* (2013.01); *A61B 1/018* (2013.01)

(58) Field of Classification Search
    CPC . A61B 1/00137; A61B 1/00098; A61B 1/018; A61B 1/00101; A61B 1/273;
    (Continued)

(56) References Cited

U.S. PATENT DOCUMENTS

| 4,689,184 | A | | 8/1987 | Plummer |
| 5,569,157 | A | * | 10/1996 | Nakazawa ......... A61B 1/00098 |
| | | | | 600/106 |

(Continued)

FOREIGN PATENT DOCUMENTS

| CN | 105982635 A | 10/2016 |
| CN | 106102542 A | 11/2016 |

(Continued)

OTHER PUBLICATIONS

International Preliminary Report on Patentability and Written Opinion of the International Searching Authority (Forms PCT/IB/326, PCT/IB/373, and PCT/ISA/237) for International Application No. PCT/JP2020/030874, dated Mar. 3, 2022, with an English translation.

(Continued)

*Primary Examiner* — Anh Tuan T Nguyen
*Assistant Examiner* — Shankar Raj Ghimire
(74) *Attorney, Agent, or Firm* — Birch, Stewart, Kolasch & Birch, LLP

(57) ABSTRACT

Provided is an endoscope including a cap that can suppress deformation due to a load and that is easily removable. The endoscope incudes a distal-end-portion body and a cap that is removably attached to the distal-end-portion body and that has an open window. The cap includes a cantilever piece that is formed on a wall portion on at least one of sides facing each other with the open window therebetween and that elastically bends, the cantilever piece having a fixed end and a free end and the cantilever piece including a stopper-target portion that is provided at the free end. The distal-end-portion body includes a stopper portion on a side facing the cantilever piece, the stopper portion engaging with the stopper-target portion. The stopper-target portion is removable from the stopper portion.

10 Claims, 15 Drawing Sheets

(58) Field of Classification Search
CPC ............ A61B 1/00064; A61B 1/00131; A61B 1/0051; A61B 1/015; A61B 1/04; A61B 1/0661; A61B 1/126
See application file for complete search history.

(56) References Cited

U.S. PATENT DOCUMENTS

| | | | |
|---|---|---|---|
| 5,860,913 A * | 1/1999 | Yamaya | A61B 1/018 600/125 |
| 5,971,733 A | 10/1999 | Huang | |
| 9,748,724 B2 | 8/2017 | Sato | |
| 11,096,558 B2 * | 8/2021 | Yamaya | G02B 23/26 |
| 2001/0003688 A1 | 6/2001 | Kondo | |
| 2002/0037140 A1 | 3/2002 | Ishibashi et al. | |
| 2007/0270638 A1 * | 11/2007 | Kitano | A61B 1/00098 600/114 |
| 2008/0212908 A1 | 9/2008 | Mori et al. | |
| 2010/0084774 A1 | 4/2010 | Liu | |
| 2011/0288372 A1 | 11/2011 | Petersen | |
| 2012/0319245 A1 | 12/2012 | Low | |
| 2015/0091206 A1 | 4/2015 | Sato | |
| 2016/0270633 A1 * | 9/2016 | Iwasaka | A61B 1/00098 |
| 2016/0270635 A1 * | 9/2016 | Tanaka | A61B 1/00098 |
| 2017/0000317 A1 * | 1/2017 | Iizuka | A61B 1/0615 |
| 2017/0020370 A1 | 1/2017 | Yamaya | |
| 2017/0238789 A1 * | 8/2017 | Iizuka | A61B 1/018 |
| 2018/0092514 A1 * | 4/2018 | Yamaya | A61B 1/00137 |
| 2018/0116491 A1 * | 5/2018 | Yamaya | A61B 90/04 |
| 2018/0140171 A1 * | 5/2018 | Yamaya | A61B 1/00062 |
| 2018/0153377 A1 | 6/2018 | Kodama | |
| 2018/0228348 A1 * | 8/2018 | Yamaya | G02B 23/16 |
| 2018/0249894 A1 * | 9/2018 | Kolberg | A61B 1/00101 |
| 2018/0317741 A1 * | 11/2018 | Yamaya | G02B 23/24 |
| 2018/0317742 A1 * | 11/2018 | Yamaya | A61B 1/00098 |
| 2019/0015172 A1 * | 1/2019 | Yamaya | A61B 90/03 |
| 2019/0117045 A1 * | 4/2019 | Hosogoe | A61B 1/00 |
| 2019/0142242 A1 * | 5/2019 | Yamaya | A61B 1/00089 600/101 |
| 2019/0223692 A1 | 7/2019 | Nakagawa | |
| 2020/0008658 A1 * | 1/2020 | Hayakawa | A61B 1/0011 |
| 2020/0352423 A1 * | 11/2020 | Hayakawa | A61B 1/00098 |
| 2022/0167835 A1 * | 6/2022 | Harada | A61B 1/00101 |

FOREIGN PATENT DOCUMENTS

| | | |
|---|---|---|
| CN | 106999007 A | 8/2017 |
| CN | 107847114 A | 3/2018 |
| CN | 108024700 A | 5/2018 |
| JP | 6-315459 A | 11/1994 |
| JP | 6-319692 A | 11/1994 |
| JP | 7-148104 A | 6/1995 |
| JP | 7-163514 A | 6/1995 |
| JP | 8-252210 A | 10/1996 |
| JP | 9-75300 A | 3/1997 |
| JP | 9-103415 A | 4/1997 |
| JP | 10-99266 A | 4/1998 |
| JP | 11-299728 A | 11/1999 |
| JP | 2001-249250 A | 9/2001 |
| JP | 2010-273727 A | 12/2010 |
| JP | 2012-40258 A | 3/2012 |
| JP | 2012-51006 A | 3/2012 |
| JP | 2016-174819 A | 10/2016 |
| JP | 2018-68834 A | 5/2018 |
| JP | 2018-517440 A | 7/2018 |
| WO | WO 2016/027574 A1 | 2/2016 |
| WO | WO 2018/016484 A1 | 1/2018 |

OTHER PUBLICATIONS

International Search Report (Form PCT/ISA/210) for International Application No. PCT/JP2020/030874, dated Oct. 20, 2020, with an English translation.

Chinese Office Action and Search Report for Chinese Application No. 202080057802.X, dated Jan. 12, 2024, with an English translation.

Japanese Decision of Refusal for Japanese Application No. 2021-540764, dated Oct. 23, 2023, with an English translation.

International Preliminary Report on Patentability (Form PCT/IPEA/409) for International Application No. PCT/JP2020/030873, dated Jul. 7, 2021, with an English translation.

International Search Report (Form PCT/ISA/210) for International Application No. PCT/JP2020/030873, dated Oct. 20, 2020, with an English translation.

Japanese Notice of Reasons for Refusal for Japanese Application No. 2021-540764, dated May 22, 2023, with an English translation.

Chinese Office Action and Search Report for corresponding Chinese Application No. 202080057798.7, dated Oct. 14, 2024, with an English translation.

Machine translation of JP-2012-040258-A, published on Mar. 1, 2012.

U.S. Office Action for U.S. Appl. No. 17/675,886, dated Oct. 23, 2024.

U.S. Office Action for U.S. Appl. No. 17/675,886, dated Aug. 2, 2024.

* cited by examiner

FIG. 2
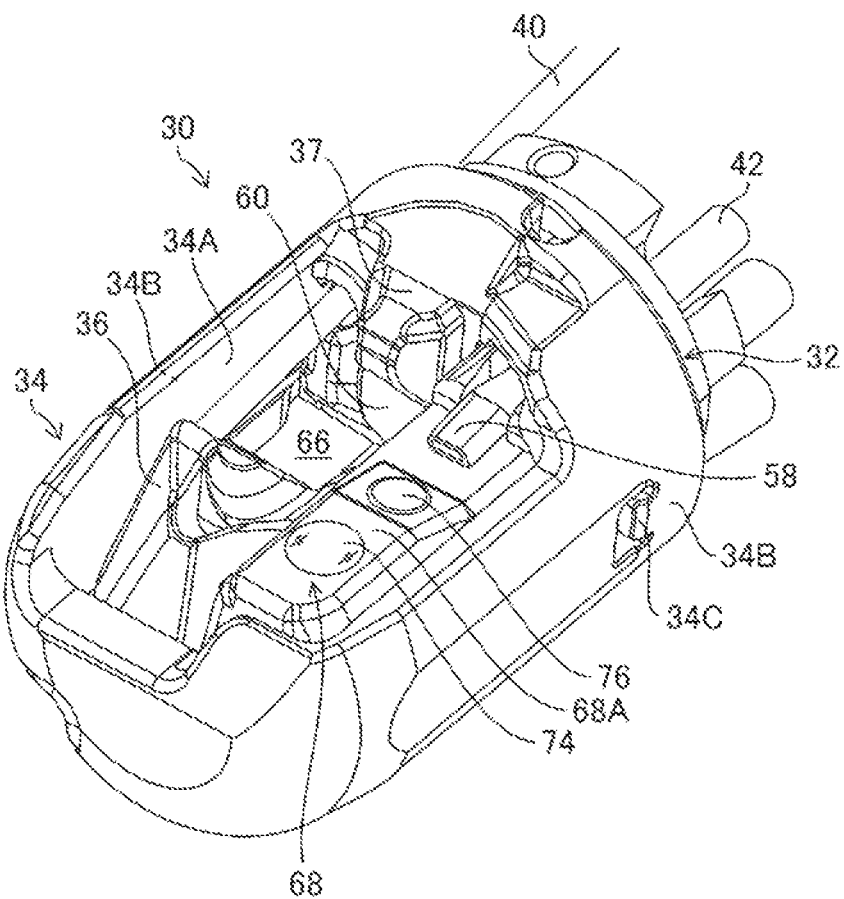
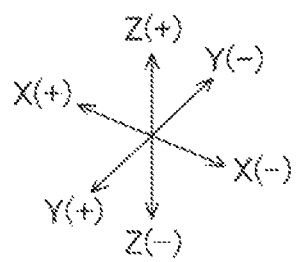

FIG. 3
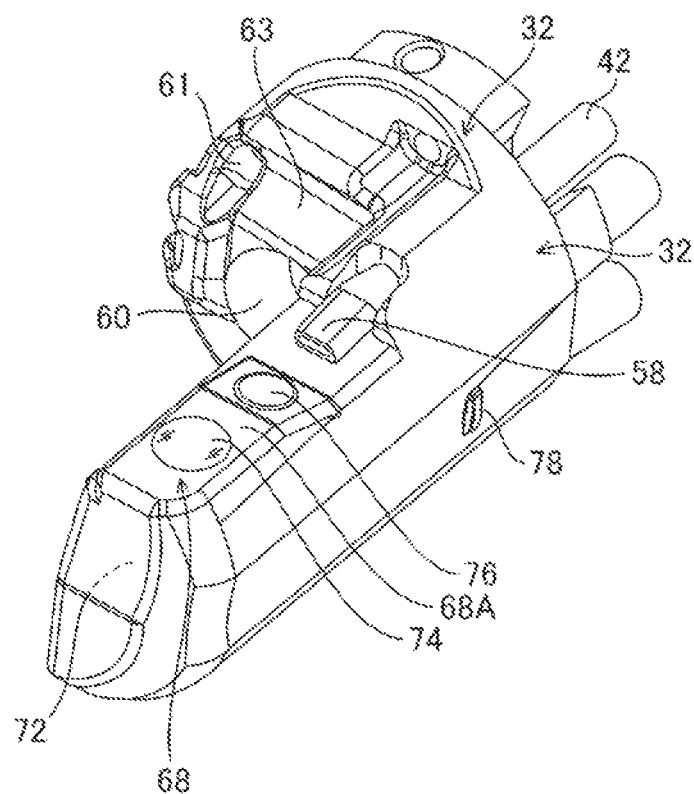
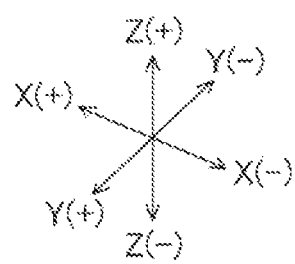

FIG. 4
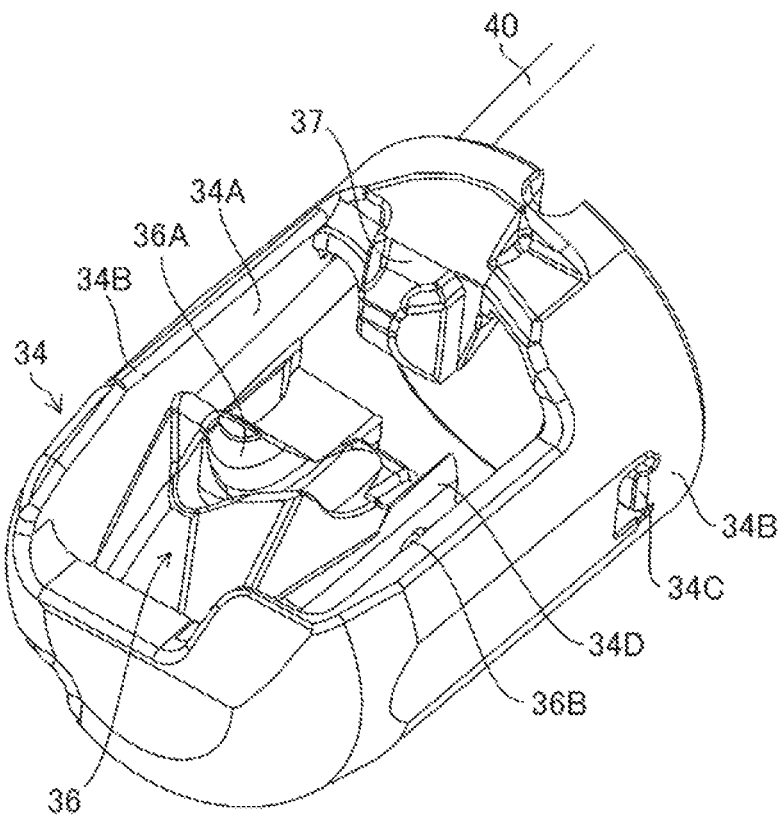
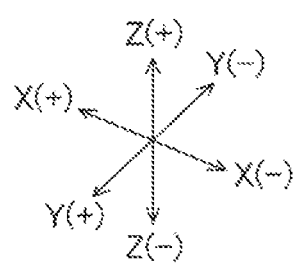

FIG. 5
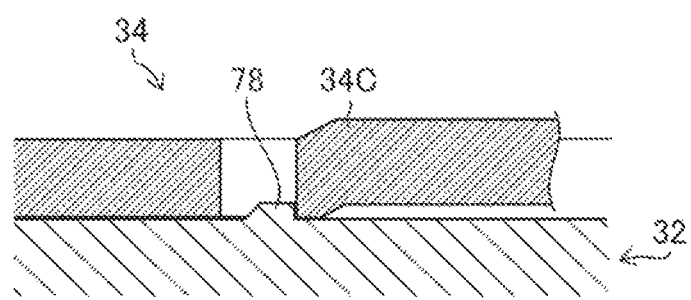
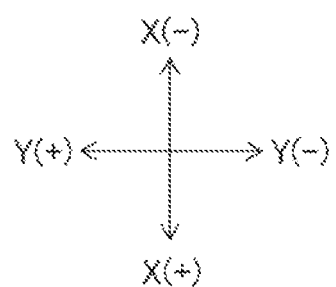

FIG. 6
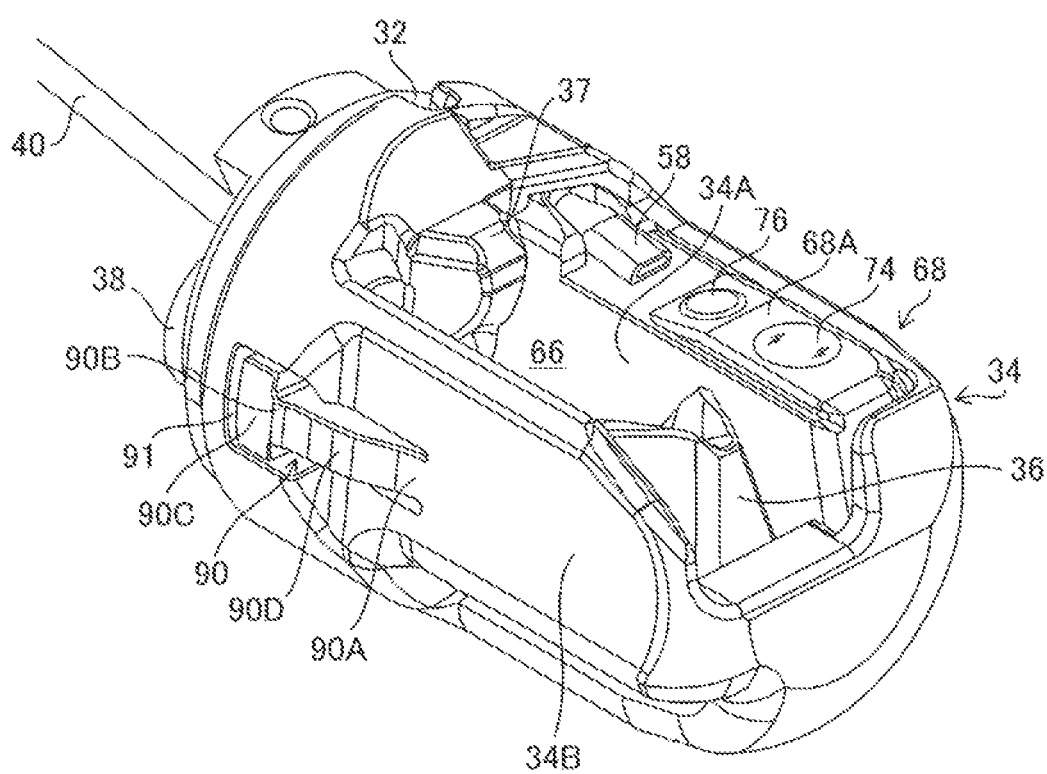
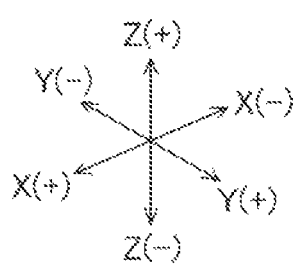

ENDOSCOPE WITH REMOVABLE CAP

CROSS-REFERENCE TO RELATED APPLICATIONS

The present application is a Continuation of PCT International Application No. PCT/JP2020/030874 filed on Aug. 14, 2020 claiming priority under 35 U.S.C § 119(a) to Japanese Patent Application No. 2019-151976 filed on Aug. 22, 2019. Each of the above applications is hereby expressly incorporated by reference, in its entirety, into the present application.

BACKGROUND OF THE INVENTION

1. Field of the Invention

The present invention relates to an endoscope, and, in particular, to an endoscope including an elevator, for changing the lead-out direction of a treatment tool, on the distal end side of an insertion section.

2. Description of the Related Art

With an endoscope, a treatment tool of an appropriate type is inserted from a treatment-tool insertion port that is formed in an operation section, and the treatment tool is used for treatment by leading out the treatment tool to the outside from a treatment-tool lead-out port that is formed in a distal end portion of an insertion section. For example, a treatment tool such as a guidewire or an imaging cannula is used with a duodenum scope. A treatment tool such as a puncture needle is used with an ultrasonic endoscope. A treatment tool such as forceps, a snare, or the like is used with other straight-viewing endoscopes and oblique-viewing endoscopes. In order to treat a desirable position in a subject with such a treatment tool, it is necessary to change the lead-out direction at the distal end portion. Therefore, an elevator for changing the lead-out direction of the treatment tool is provided in a distal-end-portion body of the distal end portion. In the endoscope, a treatment-tool-elevating mechanism for displacing the position of the elevator between an elevated position and a lowered position is provided. Moreover, a cap is removably attached to the distal-end-portion body.

An endoscope described in JP1996-252210A (JP-H08-252210A) has engageable protruding/recessed portions in a cap and in a distal-end-portion body. The cap and the distal-end-portion body are aligned and fixed to each other by engaging the protruding/recessed portions. Engagement between the protruding/recessed portions is released by pressing the cap in the up-down direction.

An endoscope described in JP2010-273727A is a side-viewing endoscope in which a cut-out surface is formed by partially cutting out a side of a distal end portion. Positional displacement of a cap is prevented by engaging an engagement groove, which is formed in a region on the proximal end side of the cut-out surface, with an engagement protrusion of the cap.

SUMMARY OF THE INVENTION

A load is applied to the cap, for example, when a treatment tool is being elevated or when a guidewire is being pulled out and fixed. It is required that the cap deform only slightly due to the load. On the other hand, it is required that the cap be deformed by a finger when removing the cap.

The present invention has been made against such a background, and an object thereof is to provide an endoscope including a cap that suppresses deformation due to a load and that can be easily removed.

An endoscope according to a first aspect of the present invention includes: an operation section in which an operation member is provided; an insertion section that is provided on a distal end side of the operation section and that is to be inserted into a subject; a distal-end-portion body that is positioned at a distal end of the insertion section, that has a treatment-tool lead-out port; an elevator that is disposed on the distal end side of the treatment-tool lead-out port and that is rotatable between a lowered position and an elevated position around a rotation shaft that is perpendicular to a longitudinal-axis direction of the insertion section; and a cap that is removably attached to the distal-end-body and that has a wall portion that defines an open window in a direction perpendicular to the longitudinal-axis direction of the insertion section and to the rotation shaft. The cap includes a cantilever piece that is formed on the wall portion on at least one of sides facing each other with the open window therebetween and that elastically bends, the cantilever piece having a fixed end and a free end and the cantilever piece including a stopper-target portion that is provided at the free end. The distal-end-portion body includes a stopper portion on a side facing the cantilever piece, the stopper portion engaging with the stopper-target portion. The stopper-target portion is removable from the stopper portion. With the first aspect, it is possible to easily remove the cap and to prevent deformation due to a load.

In an endoscope according to a second aspect of the present invention, the cantilever piece includes a pressing portion that is positioned between the fixed end and the free end and that is separated from the distal-end-portion body, the distal-end-portion body has a fulcrum portion at a position facing a part of the cantilever piece between the pressing portion and the free end, and, by pressing the pressing portion toward the distal-end-portion body, the cantilever piece is bent with the fulcrum portion as a fulcrum to release engagement between the stopper portion and the stopper-target portion.

In an endoscope according to a third aspect of the present invention, the fulcrum portion is disposed on the distal end side of the distal-end-portion body from a position of the stopper portion, and the fixed end of the cantilever piece is disposed on the distal end side of the distal-end-portion body relative to a position of the fulcrum portion.

In an endoscope according to a fourth aspect of the present invention, the stopper-target portion has a width greater than a width of any other part of the cantilever piece, the stopper portion is narrower than the stopper-target portion, and the stopper portion is formed of a member that defines a groove portion that is wider than any other part of the cantilever piece.

In an endoscope according to a fifth aspect of the present invention, the fulcrum portion is disposed at a position on a proximal end side of the distal-end-portion body relative to a position of the stopper portion, and the fixed end of the cantilever piece is disposed on the proximal end side of the distal-end-portion body relative to the position of the fulcrum portion.

In an endoscope according to a sixth aspect of the present invention, the cap includes, in the wall portion on which the cantilever piece is formed, a notch that is perpendicular to the cantilever piece and a small-thickness portion that is parallel to the cantilever piece, and, by deforming the cap along the small-thickness portion, the cap is broken at the notch to release engagement between the stopper portion and the stopper-target portion.

In an endoscope according to a seventh aspect of the present invention, the stopper portion has an inclined surface that spreads outward from the distal end side toward a proximal end side of the distal-end-portion body.

In an endoscope according to an eighth aspect of the present invention, a contact member is provided at a position facing a treatment-tool guiding surface of the elevator when the elevator is in the elevated position.

In an endoscope according to a ninth aspect of the present invention, the cap and the contact member are formed of an integrally molded body.

In an endoscope according to a tenth aspect of the present invention, the elevator is attached to the cap so as to be rotatable around the rotation shaft.

With the endoscope according to the present invention, it is possible to provide an endoscope including a cap that suppresses deformation due to a load and that can be easily removed.

BRIEF DESCRIPTION OF THE DRAWINGS

FIG. 2 is an enlarged perspective view of a distal end portion;

FIG. 3 is a perspective view of a distal-end-portion body according to the first embodiment illustrated in FIG. 2;

FIG. 4 is a perspective view of a cap illustrated in FIG. 2;

FIG. 5 is a sectional view including a cap-side latch portion illustrated in FIG. 2;

FIG. 6 is a perspective view of the distal end portion according to the first embodiment as seen from the X(+) side;

DESCRIPTION OF THE PREFERRED EMBODIMENTS

Hereafter, endoscopes according to preferred embodiments of the present invention will be described with reference to the drawings.

First Embodiment

Figure 1:
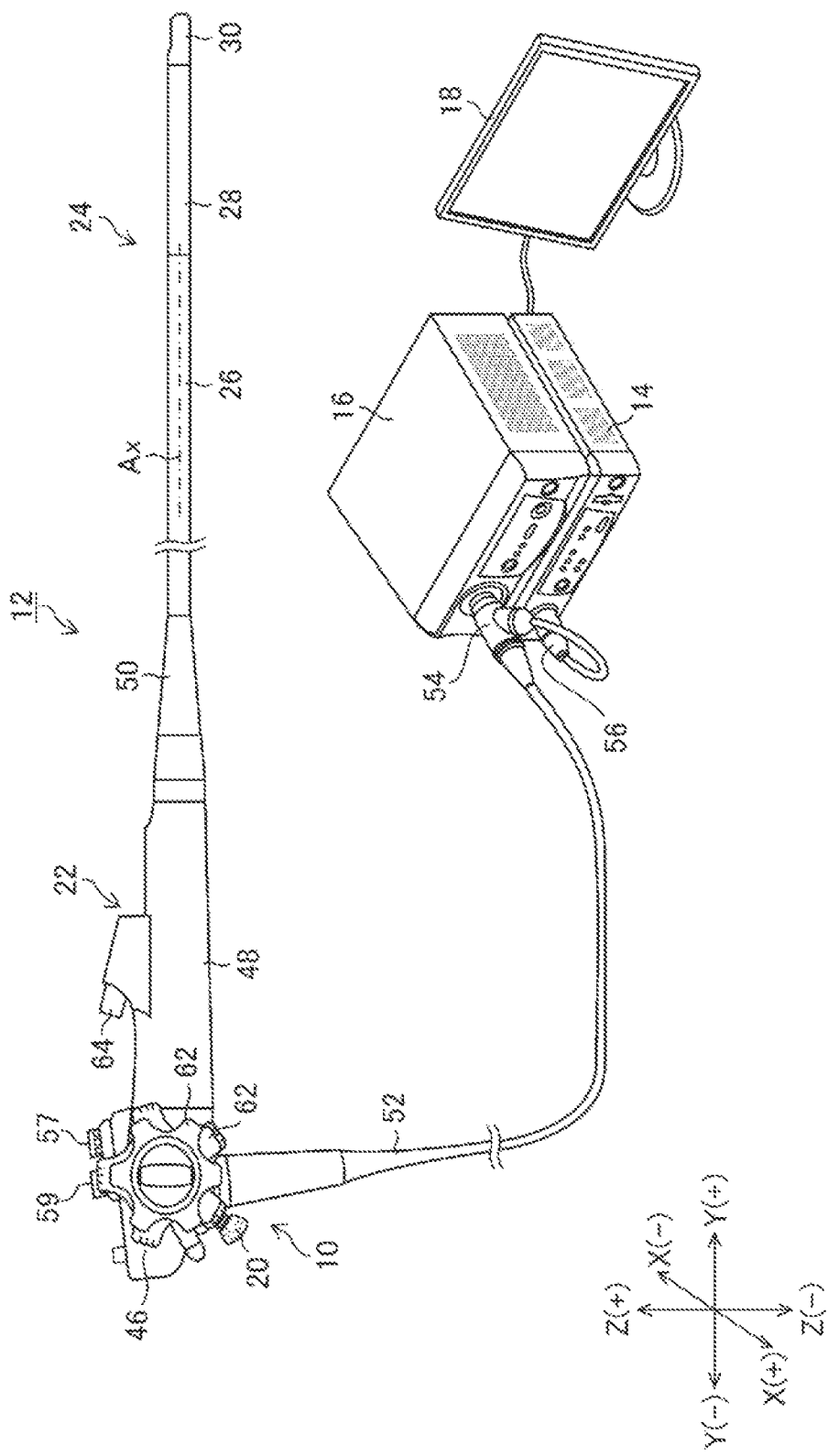
FIG. 1 illustrates the configuration of an endoscope system including an endoscope according to a first embodiment.

FIG. 1 illustrates the configuration of an endoscope system 12 including an endoscope 10 according to an embodiment of the present invention. The endoscope system 12 includes the endoscope 10, a processor device 14, a light source device 16, and a display 18.

The endoscope 10 includes: an operation section 22 in which an elevating operation lever 20, which is an operation member, is provided; and an insertion section 24, which is provided on the distal end side of the operation section 22 and which is to be inserted into a subject.

The insertion section 24 has a longitudinal-axis direction Ax extending from the proximal end toward the distal end; and includes a flexible portion 26, a bending portion 28, and a distal end portion 30, sequentially from the proximal end toward the distal end. First, schematic configuration of the distal end portion 30 will be described, and then detailed configuration of the distal end portion 30 will be described.

FIG. 2 is an enlarged perspective view of the distal end portion 30. Here, the endoscope 10 according to the embodiment (see FIG. 1) is, for example, a side-viewing endoscope used as a duodenum scope, and the distal end portion 30 of FIG. 2 has the configuration of a side-viewing endoscope.

FIG. 3 is a perspective view of a distal-end-portion body 32 of the distal end portion 30. FIG. 4 is a perspective view of a cap 34 of the distal end portion 30. As illustrated in FIG. 2, the distal end portion 30 has the distal-end-portion body 32 and the cap 34. The cap 34 is removably attached to the distal-end-portion body 32. The distal-end-portion body 32 is provided on the distal end side of the insertion section 24 (see FIG. 1). In the distal-end-portion body 32, an elevator 36, which has a treatment-tool guiding surface 36A described below, is provided. FIGS. 2 and 4 illustrate a state in which the elevator 36 is located in a lowered position.

FIG. 2 also illustrates various elements that are placed inside the insertion section 24 of the endoscope 10 (see FIG. 1). To be specific, provided are the following: the elevator 36 for performing, on a distal end portion of a treatment tool (not shown), an operation of changing the lead-out direction of the distal end portion of the treatment tool that is led out from the distal-end-portion body 32; an elevating operation wire 40 (hereafter, referred to as "wire 40"); and an air/water supply tube 42. The wire 40 is directly coupled to the elevator 36. Although not illustrated in FIG. 2, the following contents are also provided: a treatment tool channel 38 leading to the distal-end-portion body 32 (see FIG. 6); an angle wire for performing an operation of changing the bending direction of the bending portion 28 (see FIG. 1); a signal cable for transmitting an image signal; a light guide for transmitting illumination light; and the like.

In the present specification, a three-dimensional orthogonal coordinate system having a triaxial direction (X-axis direction, Y-axis direction, Z-axis direction) will be used for description. That is, as seen from the operation section 22 toward the distal end portion 30, when the direction in which the treatment tool (not shown) is led out by the elevator 36 is defined as the upward direction, the upward direction is defined as the Z(+) direction, and the downward direction, which is opposite to the upward direction, is defined as the Z(−) direction. The rightward direction at this time is defined as the X(+) direction, and the leftward direction is defined as the X(−) direction. The forward direction at this time (direction toward the distal end side in the longitudinal-axis direction Ax of the insertion section 24) is defined as the Y(+) direction, and the backward direction (direction toward the proximal end side in the longitudinal-axis direction Ax of the insertion section 24) is defined as the Y(−) direction. The Y-axis direction, including the Y(+) direction and the Y(−) direction, is parallel to the longitudinal-axis direction Ax of the insertion section 24. The Z-axis direction is a direction perpendicular to the longitudinal-axis direction Ax. The X-axis direction is a direction perpendicular to the Z-axis direction.

Referring back to FIG. 1, the operation section 22 as a whole has a substantially cylindrical shape. The operation section 22 includes an operation section body 46 on which the elevating operation lever 20 is rotatably provided, and a grip portion 48 that is continuously connected to the operation section body 46. A proximal end portion of the insertion section 24 is provided on the distal end side of the grip portion 48 via a breakage preventing tube 50. The grip portion 48 is a portion to be gripped by an operator when the operator operates the endoscope 10.

The operation section body 46 is equipped with a universal cable 52. A light source connector 54 is provided on the distal end side of the universal cable 52. An electric connector 56 branches from the light source connector 54. The electric connector 56 is connected to the processor device 14, and the light source connector 54 is connected to the light source device 16.

On the operation section body 46, an air/water supply button 57 and a suction button 59 are arranged side by side. When the air/water supply button 57 is operated, air and water are supplied to the air/water supply tube 42 of FIG. 2, and the air and water can be ejected from an air/water supply nozzle 58 provided in the distal-end-portion body 32. The air/water supply button 57 of FIG. 1 is operated in two steps. With an operation in the first step, air is supplied to the air/water supply tube 42. With an operation in the second step, water is supplied to the air/water supply tube 42.

When the suction button 59 of FIG. 1 is operated, a bodily fluid such as blood can be sucked from a suction opening, which also serves as a treatment-tool lead-out port 60 provided in the distal-end-portion body 32 of FIG. 2, through the treatment tool channel 38 (see FIG. 6).

As illustrated in FIG. 1, a pair of angle knobs 62, which are used to for the operation of bending the bending portion 28, is disposed on the operation section body 46. The pair of angle knobs 62 are coaxially rotatable.

The elevating operation lever 20 is rotatable coaxially with the angle knobs 62. The elevating operation lever 20 is rotated by a hand of an operator who grips the grip portion 48. When the elevating operation lever 20 is rotated, the wire 40 of FIG. 2 is pushed or pulled in synchronism with the rotational operation of the elevating operation lever 20. Due to such an operation on the wire 40, the posture of the elevator 36, which is coupled to the distal end side of the wire 40, is changed between the lowered position illustrated in FIG. 2 and the elevated position (not shown).

As illustrated in FIG. 1, the grip portion 48 of the operation section 22 includes a treatment-tool insertion port 64 for inserting a treatment tool. A treatment tool (not shown), which is inserted from the treatment-tool insertion port 64 with the distal end portion thereof being a leading end portion, is inserted into the treatment tool channel 38 (not shown), and is led to the outside from the treatment-tool lead-out port 60 provided in the distal-end-portion body 32.

As illustrated in FIG. 1, the flexible portion 26 of the insertion section 24 has a helical tube (not shown) that is formed by helically winding a thin metal strip having elasticity. The flexible portion 26 is formed by covering the outside of this helical tube with a tubular mesh member, which is made of a braided metal wire, and by covering the outer peripheral surface of the mesh member with an outer covering made of a resin.

The bending portion 28 of the insertion section 24 has a structure such that a plurality of angle rings (not shown) are unrotatably coupled to each other. The bending portion 28 is formed by covering the outer periphery of this structure with a tubular mesh member made of a braided metal wire, and by covering the outer peripheral surface of the mesh member with a tubular outer covering made of rubber. For example, four angle wires (not shown) are placed from the bending portion 28, which is configured in this way, to the angle knobs 62. When the angle knobs 62 are rotated, these angle wires are pushed or pulled, and thereby the bending portion 28 is bent in the up-down direction and in the left-right direction.

The endoscope 10 according to the embodiment is, for example, a side-viewing endoscope that is used as a duodenum scope, and the insertion section 24 is inserted into a subject through the oral cavity. The insertion section 24 is inserted from the esophagus to the duodenum through the stomach, and a predetermined operation such as a predetermined test or treatment is performed.

Examples of a treatment tool used with the endoscope 10 according to the embodiment include: biopsy forceps having a cup, which can obtain living tissue, at a distal end portion; an endoscopic sphincterotomy (EST) knife; and an imaging cannula.

Next, referring to FIGS. 2, 3, and 4, the structure of the distal end portion 30 will be described.

As illustrated in FIG. 2, the distal end portion 30 includes the distal-end-portion body 32 and the cap 34 that is removably attached to the distal-end-portion body 32. As illustrated in FIG. 3, the distal-end-portion body 32 has a partition wall 68 that protrudes in the Y(+) direction. When the cap 34 is attached to the distal-end-portion body 32, an elevator housing space 66 is formed by the partition wall 68 of the distal-end-portion body 32 and wall portions 34B of the cap 34. The elevator housing space 66 is disposed at a position in the X(+) direction of the partition wall 68 and in the Y(+) direction of the treatment-tool lead-out port 60. The distal-end-portion body 32 is made of an anticorrosive metal material.

As illustrated in FIGS. 2 and 3, in an upper surface 68A on the Z(+) side of the partition wall 68, an illumination window 74 and an observation window 76 are placed adjacent to each other in the Y direction. The observation window 76 enables observation of a field of view in the Z(+) direction.

The air/water supply nozzle 58 is provided on the distal-end-portion body 32 toward the observation window 76. The observation window 76 is cleaned with air and water ejected from the air/water supply nozzle 58.

As illustrated in FIG. 3, the partition wall 68 includes an optical-system housing chamber 72 inside thereof. The optical-system housing chamber 72 houses an illumination unit (not shown) and an imaging unit (not shown). The illumination unit includes an illumination lens (not shown), which is disposed on the optical-system housing chamber 72 side of the illumination window 74, and a light guide (not shown), which is disposed so that a distal end surface thereof faces the illumination lens. The light guide is placed into the universal cable 52 from the insertion section 24 of the endoscope 10 (see FIG. 1) through the operation section 22. A proximal end of the light guide is connected to the light source connector 54. When the light source connector 54 is connected to the light source device 16, irradiation light from the light source device 16 is transmitted to the illumination lens through the light guide. A field of view in the Z(+) direction is irradiated with irradiation light from the illumination window 74.

The imaging unit includes an imaging optical system (not shown), which is placed inside the observation window 76, and an image pick-up element (not shown) of a complementary metal oxide semiconductor (CMOS) type or a charge coupled device (CCD) type. A distal end of a signal cable (not shown) is connected to the image pick-up element. The signal cable is placed into the universal cable 52 from the insertion section 24 of the endoscope 10 (see FIG. 1) through the operation section 22. A proximal end of the signal cable is connected to the electric connector 56. When the electric connector 56 is connected to the processor device 14, an image pick-up signal of a subject image obtained by the imaging unit is transmitted to the processor device 14 through the signal cable. The image pick-up signal is image-processed by the processor device 14 and then displayed on the display 18 as a subject image.

The distal-end-portion body 32 has a stopper portion 63 on the proximal end side thereof. The stopper portion 63 engages with a stopper-target portion (described below) that is provided on a surface of a contact member 37 on the proximal end side. In the distal-end-portion body 32, a through-hole 61, for inserting the wire 40 (not shown) therethrough, is formed.

As illustrated in FIG. 4, the cap 34 includes the wall portion 34B that has a substantially tubular shape whose distal end side is sealed. In a part of the outer peripheral surface of the cap 34, an open window 34A having a substantially rectangular shape is defined by the wall portion 34B. A bearing 34D, which extends in the Y(+) direction (direction extending in the longitudinal-axis direction Ax), is formed inside the cap 34. The bearing 34D has a plate-like shape having a height in the Z(+) direction. The cap 34 is made of an elastic material that is, for example, a rubber material, such as fluorocarbon rubber or silicone rubber, or a resin material, such as polysulfone or polycarbonate.

A rotation shaft 36B of the elevator 36 is supported in a through-hole (not shown) of the bearing 34D. The rotation shaft 36B is a rod-shaped member having a length in the X-axis direction perpendicular to the bearing 34D. The elevator 36 is rotatable between a lowered position and an elevated position around the rotation shaft 36B.

The wire 40 is coupled to the elevator 36. The wire 40 is attached to a position that is adjacent to the treatment-tool guiding surface 36A and that is on a side opposite to a side on which the rotation shaft 36B is formed on the distal end side of the elevator 36.

In the present embodiment, the elevator 36 is attached to the cap 34 illustrated in FIG. 4, and the cap 34 with the elevator 36 is used as a single component as a whole. The wire 40 is coupled to the elevator 36.

The open window 34A of the cap 34 opens in the Z(+) direction. That is, the opening direction of the open window 34A of the cap 34 is a direction that is perpendicular to the longitudinal-axis direction Ax of the insertion section and that is perpendicular to the axial direction of the rotation shaft 36B (X-axis direction).

The cap 34 is an integrally molded body in which the wall portion 34B and the contact member 37 are integrally molded. The contact member 37 is made of a resin material. The contact member 37 is disposed on the proximal end side of the open window 34A. The contact member 37 as a whole protrudes in the Y(+) direction. The phrase "integrally mold" means integrally molding a product (the cap 34 and the contact member 37) at the same a time as joining of members, without using adhesives or mechanical joint.

The cap 34, including the wire 40 and the elevator 36, is removed from the distal-end-portion body 32 after a treatment using the endoscope 10 is finished, and, for example, is thrown away as a disposable item.

When the cap 34 is attached to the distal-end-portion body 32, as illustrated in FIG. 2, the cap 34 forms the elevator housing space 66, and the open window 34A opens in the Z(+) direction. The treatment-tool lead-out port 60 of the distal-end-portion body 32 communicates with the open window 34A through the elevator housing space 66. The contact member 37 is positioned in the Z(+) direction with respect to the treatment-tool lead-out port 60, and the contact member 37 is provided at a position facing the treatment-tool guiding surface 36A when the elevator 36 is in the elevated position.

The distal end portion 30 includes a removal-preventing mechanism for preventing the cap 34 from becoming removed from the distal-end-portion body 32 in the Y(+) direction. The removal-preventing mechanism includes: in the cap 34, a cap-side latch portion 34C (see FIGS. 2 and 4) that is provided in one of the two wall portions 34B, which are located with the open window 34A therebetween; and, in the distal-end-portion body 32, a body-side latch portion 78 (see FIG. 3) that is provided at a position facing the cap-side latch portion 34C.

As illustrated in FIGS. 2 and 4, the cap-side latch portion 34C is formed by cutting out the cap 34 in a U-shape. The U-shaped cutout extends through the outside and the inside of the cap 34. The U-shaped cutout has a U-shape that opens in the Y(−) direction, and the cap-side latch portion 34C is in a state, which is a so-called cantilever state, in which a side of the cap-side latch portion 34C on the proximal end side is coupled to the cap 34. The distal end side of the cap-side latch portion 34C is displaceable in the X(+) direction and the X(−) direction with a coupling position with the cap 34 as a fulcrum. As illustrated in FIG. 3, the body-side latch portion 78 is a protrusion that is formed on the distal-end-portion body 32 and that protrudes in the X(−) direction.

FIG. 5 is a sectional view including the cap-side latch portion 34C illustrated in FIG. 2. The cap 34 and the distal-end-portion body 32 are attached to or removed from each other by being moved relative to each other in the Y-axis direction. The body-side latch portion 78 has a substantially trapezoidal shape in the sectional view. The body-side latch portion 78 has, on the distal end side thereof, an inclined surface that spreads outward from the distal end side toward the proximal end side of the distal-end-portion body 32. On the other hand, the body-side latch portion 78 has, on the proximal end side thereof, a perpendicular surface that is perpendicular to the Y-axis direction. The cap-side latch portion 34C has, on the distal end side thereof, an inwardly bent shape, and the distal end of the cap-side latch portion 34C is formed of a perpendicular surface that is perpendicular to the Y-axis direction.

A case of attaching the cap 34 to the distal-end-portion body 32 will be described. In the following description, for ease of understanding, it is assumed that the distal-end-portion body 32 is in a state of being fixed.

When the cap 34 is being attached to the distal-end-portion body 32, the cap 34 is moved in the direction from Y(+) to Y(−). The bent portion of the cap-side latch portion 34C comes into contact with the inclined surface of the body-side latch portion 78. When the cap 34 is moved further in the Y(−) direction, the cap-side latch portion 34C moves along the inclined surface of the body-side latch portion 78, and, finally, moves over the body-side latch portion 78.

The distal end of the cap-side latch portion 34C and the proximal end of the body-side latch portion 78 each have a perpendicular surface. When the cap 34 moves in the Y(+) direction, a large resistance force is generated as the cap-side latch portion 34C moves over the body-side latch portion 78. Removal of the cap 34 from the distal-end-portion body 32 is suppressed.

Figure 7:
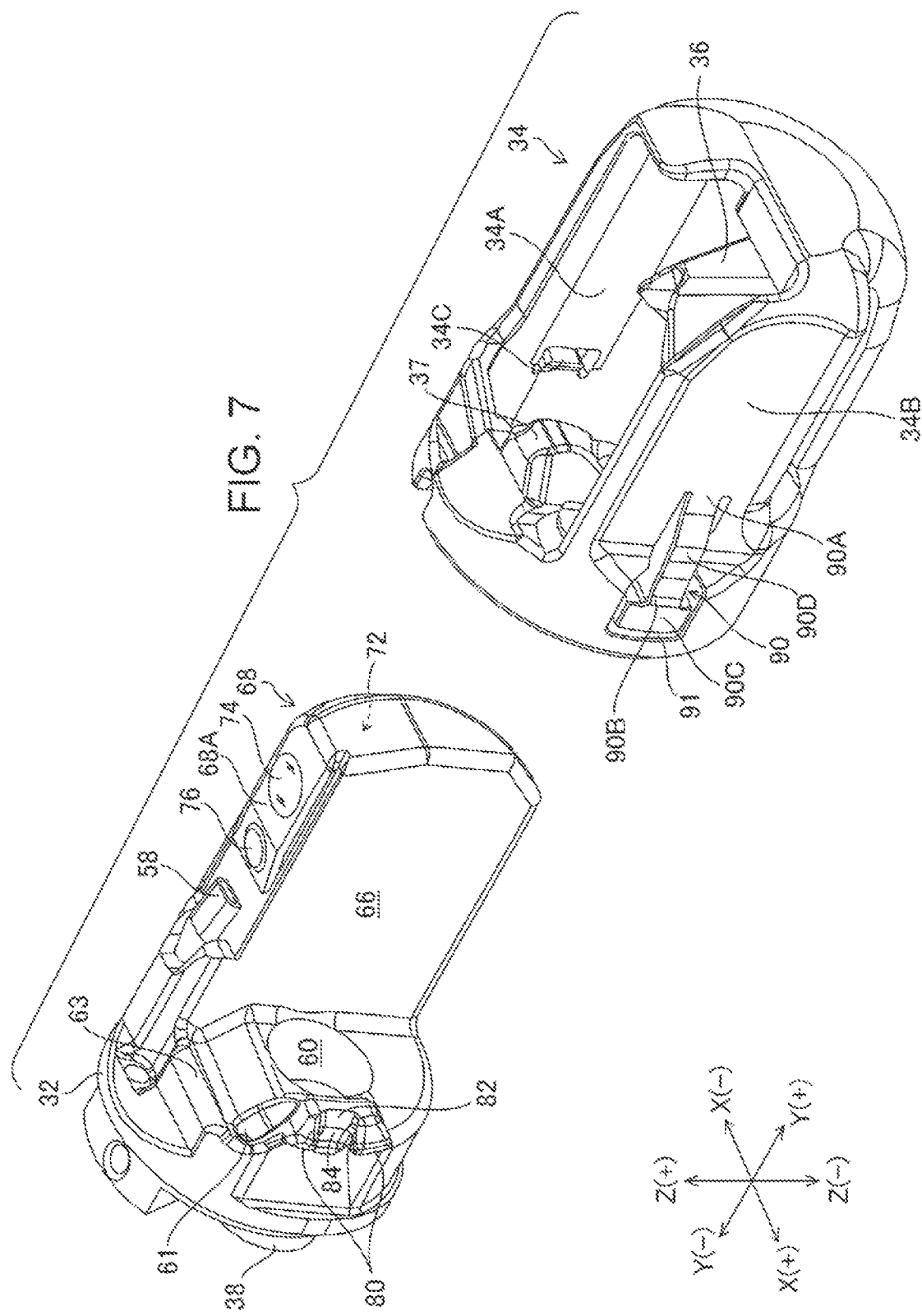
FIG. 7 is a perspective assembly view of the distal end portion illustrated in FIG. 6.
Figure 8:
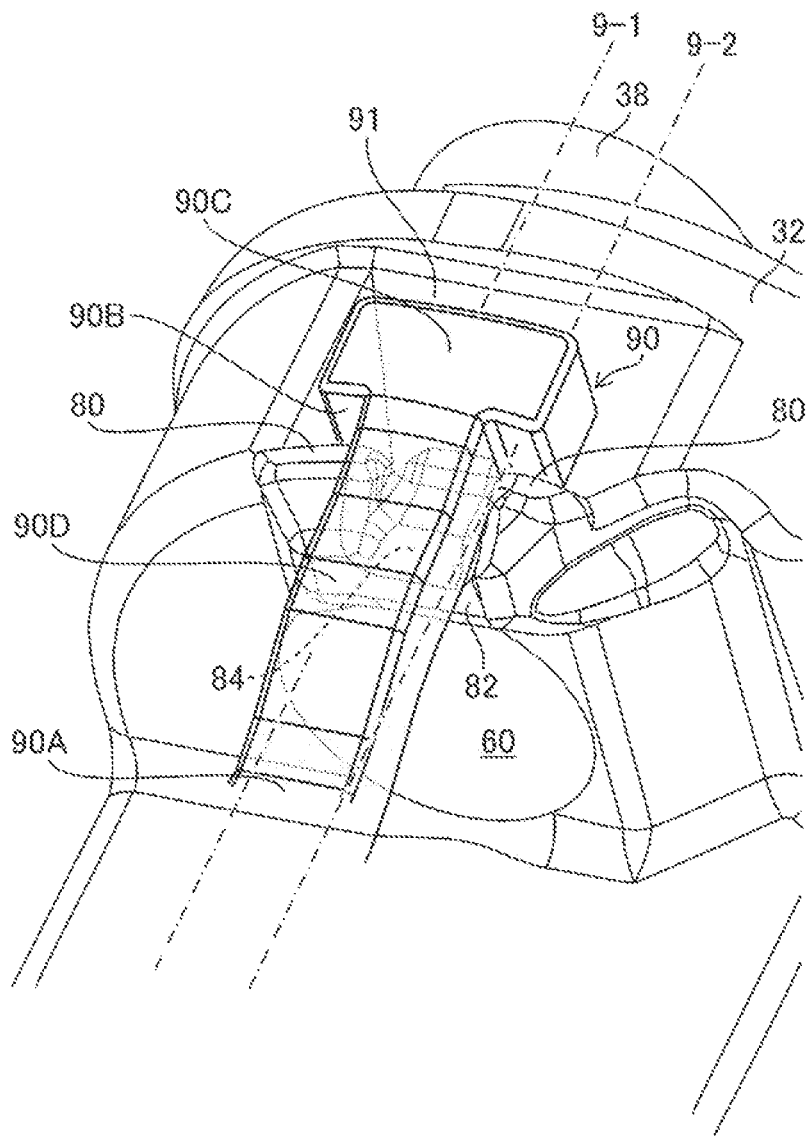
FIG. 8 is a partial enlarged perspective view of the distal end portion.
Figure 9:
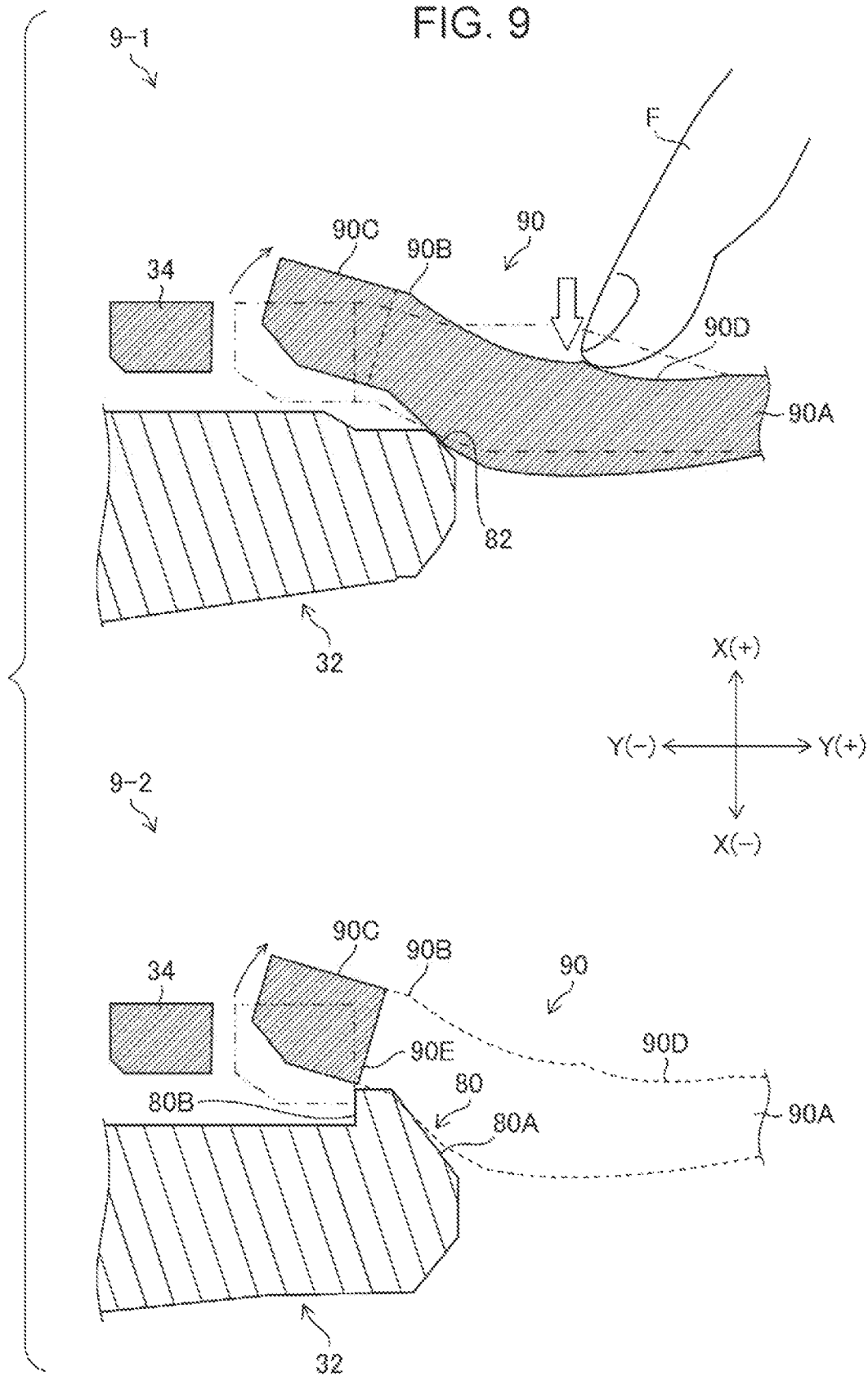
FIG. 9 illustrates an operation of attaching the cap to the distal-end-portion body and an operation of removing the cap from the distal-end-portion body according to the first embodiment.

Next, referring to FIGS. 6 to 9, an endoscope including the cap 34, which can suppress deformation due to a load and which is easily removable from the distal-end-portion body 32, will be described. FIG. 6 is a perspective view of the distal end portion 30 as seen from the X(+) side, and FIG. 7 is a perspective assembly view of the distal end portion 30. FIG. 8 is a partial enlarged perspective view of the distal end portion 30. FIG. 9 illustrates operations of attaching and removing the cap. In FIG. 7, the wire 40 is not illustrated.

As illustrated in FIGS. 6 and 7, the cap 34 has a cantilever piece 90 that is provided on one of the two wall portions 34B, which are disposed in the X(+) direction and the X(−) direction with the open window 34A therebetween. The cantilever piece 90 is formed by providing a cutout 91 in the cap 34. The cutout 91 extends through the outside and the inside of the cap 34.

The cantilever piece 90 extends in the Y-axis direction and has a fixed end 90A, which is coupled to the cap 34, and a free end 90B, which is not coupled to the cap 34. The fixed end 90A is positioned on the distal end side (in the Y(+) direction) relative to the free end 90B. Because the free end 90B is not coupled to the cap 34, the free end 90B is displaceable in the X(+) direction and the X(−) direction. The free end 90B is movable. Because the cantilever piece 90 is formed by the cutout 91 of the cap 34, the cantilever piece 90 is made of the same material as the cap 34.

A stopper-target portion 90C is provided at the free end 90B of the cantilever piece 90. The stopper-target portion 90C has a width that is greater than the width of any other part of the cantilever piece 90. When the stopper-target portion 90C is seen from the X(+) direction, the cantilever piece 90 as a whole is T-shaped. The stopper-target portion 90C is displaceable in the X(+) direction and the X(−) direction in conjunction with the free end 90B.

The cantilever piece 90 has a pressing portion 90D that is positioned between the fixed end 90A and the free end 90B and that is separated from the distal-end-portion body 32. When a pressing force due to a human finger (not shown) is applied to the pressing portion 90D, the pressing portion 90D becomes elastically bent toward the X(−) side. The shape of the cantilever piece 90 is not limited to the T-shape, as long as the cantilever piece 90 can be bent by a pressing force due to a human finger. The shape of the cantilever piece 90 is determined in consideration of length, thickness, width, and the like. The length of the cantilever piece 90 is a distance in the Y-axis direction, the thickness of the cantilever piece 90 is the distance between the outer surface and the inner surface of the cantilever piece 90, and the width of the cantilever piece 9) is a distance in a direction perpendicular to the length and the thickness.

As illustrated in FIG. 7, the distal-end-portion body 32 has two stopper portions 80 and a fulcrum portion 82, which is positioned between the stopper portions 80, on a side facing the cantilever piece 90. The two stopper portions 80 define a groove portion 84.

As illustrated in FIG. 8, the two stopper portions 80 are disposed at positions such that the stopper portions 80 form the groove portion 84 that is narrower than the width of the stopper-target portion 90C and that is wider than the width of any other part of the cantilever piece 90 (any part other than the stopper-target portion 90C). The stopper portions 80 and the stopper-target portion 90C are engaged due to the magnitude relationship among the distance between the stopper portions 80, the width of the stopper-target portion 90C, and the width of any part other than the stopper-target portion 90C.

As long as the stopper portions 80 and the stopper-target portion 90C are provided as a removal-preventing mechanism, the cap-side latch portion 34C and the body-side latch portion 78 need not be provided.

Next, referring to FIG. 9, attachment and removal of the cap 34 and the distal-end-portion body 32 will be described. 9-1 is a sectional view taken along line 9-1 of FIG. 8, and 9-2 is a sectional view taken along line 9-2 of FIG. 8.

In a state in which the cap 34 is attached to the distal-end-portion body 32, the cantilever piece 90 is not bent as shown by a two-dot chain line in 9-1. In the embodiment, the cantilever piece 90 is substantially in contact with the fulcrum portion 82. The pressing portion 90D of the cantilever piece 90 is separated from the distal-end-portion body 32. The term "separated" means a state in which the pressing portion 90D is not in contact with the distal-end-portion body 32.

As illustrated in 9-2, in the state in which the cap 34 is attached to the distal-end-portion body 32, the stopper portion 80 and the stopper-target portion 90C, which is shown by a two-dot chain line, engage with each other. As illustrated in 9-2, the stopper portion 80 has an inclined surface 80A. The inclined surface 80A is an inclined surface that spreads outward from the distal end side toward the proximal end side of the distal-end-portion body 32. The stopper portion 80 has, on the proximal end side thereof, a perpendicular surface 80B that is perpendicular to the Y-axis direction.

As illustrated in 9-1 and 9-2, the fulcrum portion 82 is disposed on the distal end side of the distal-end-portion body 32 (in the Y(+) direction) from the position of the perpendicular surface 80B (engagement surface) of the stopper portion 80. The fixed end 90A of the cantilever piece 90 is disposed on the distal end side of the distal-end-portion body 32 relative to the position of the fulcrum portion 82.

When the cap 34 is being attached to the distal-end-portion body 32, the cap 34 is moved in the direction from Y(+) to Y(−). The stopper-target portion 90C *comes* into contact with the inclined surface 80A of the stopper portion 80. When the cap 34 is moved further in the Y(−) direction, the stopper-target portion 90C moves along the inclined surface 80A of the stopper portion 80, and, finally, moves over the stopper portion 80.

The stopper-target portion 90C has, on the distal end side thereof, a perpendicular surface 90E perpendicular to the Y-axis direction. The perpendicular surface 80B of the stopper portion 80 and the perpendicular surface 90E of the stopper-target portion 90C face each other, and the stopper portion 80 and the stopper-target portion 90C engage with each other. Thus, when the cap 34 moves in the Y(+) direction, a large resistance force is generated as the stopper-target portion 90C moves over the stopper portions 80. Removal of the cap 34 from the distal-end-portion body 32 is suppressed.

The term "engage" means a state in which, as seen from the Y(+) direction, the stopper portion 80 is positioned on the distal end side, the stopper-target portion 90C is positioned on the proximal end side, and the stopper portion 80 and the stopper-target portion 90C partially overlap. In the partially overlapping state, the perpendicular surfaces need not face each other.

Next, as illustrated in 9-1, when a force in the X(−) direction is applied to the pressing portion 90D by a finger F, the cantilever piece 90, which is shown by a solid line, bends in the X(−) direction. Because the cantilever piece 90 is in contact with the fulcrum portion 82, as illustrated in 9-2, the stopper-target portion 90C, which is provided at the free end 90B, moves toward the X(+) side with the fulcrum portion 82 as a fulcrum due to "leverage". Engagement between the stopper portion 80 and the stopper-target portion 90C is released, and the stopper-target portion 90C is removed from the stopper portion 80. The cap 34 can be easily moved from the distal-end-portion body 32 in the Y(+) direction to be removed.

Figure 10:
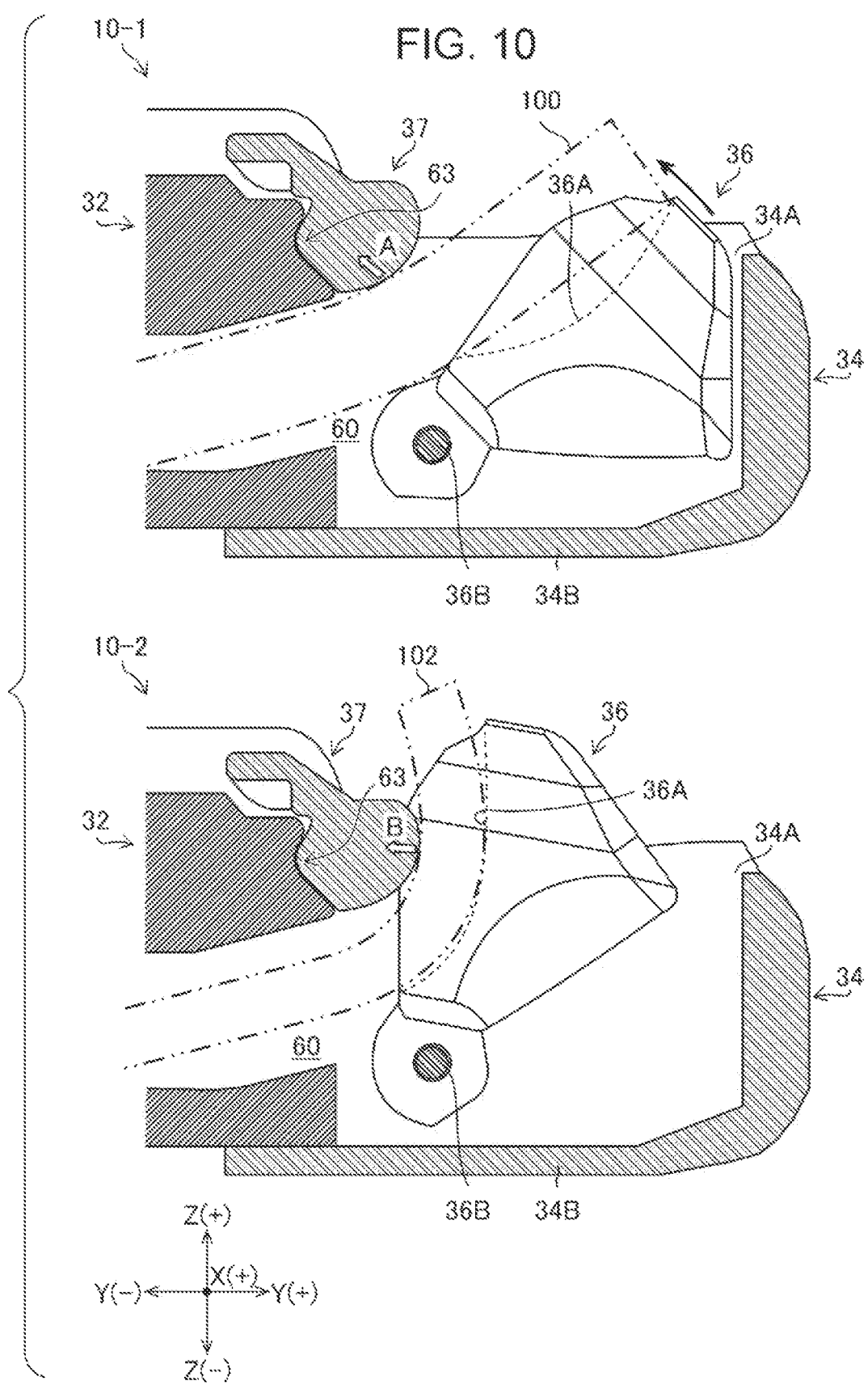
FIG. 10 illustrates a state in which a treatment tool and a guidewire are elevated by using an elevator.

The cap 34 according to the embodiment has a structure that has the contact member 37, which is integrally molded, and that supports the elevator 36. Therefore, as illustrated in 10-1 of FIG. 10, when the elevator 36 elevates a treatment tool 100, the contact member 37 receives a load in the direction A. As illustrated in 10-2, when a guidewire 102 is being locked, the contact member 37 receives a load in the direction B. Therefore, the cap 34 becomes likely to deform.

Moreover, when the elevator 36 is lowered, the wall portion 34B, which faces the open window 34A of the cap 34, also receives a load and becomes likely to deform. Accordingly, in the cap 34, a part that receives a load needs to have high rigidity to restrict deformation.

In the cap 34 according to the embodiment, the cantilever piece 90 is provided in a part that is not likely to receive a load, that is, on a side of one of the wall portions 34B, which face each other with the open window 34A therebetween. The part that is not likely to receive a load may have a rigidity lower than that of a part that receives a load. Low rigidity allows the cantilever piece 90 to easily bend when pressed by a finger. The cap 34 according to the embodiment can be easily attached and removed while maintaining rigidity.

The cap 34 according to the first embodiment has a shape that can be easily molded. When the cantilever piece 90 according to the first embodiment is being formed, a die is inserted into a portion corresponding to the cutout 91. Because the die is moved outward from the cap 34, demolding of the die can be easily performed.

Second Embodiment

Referring to the drawings, an endoscope according to a second embodiment will be described. Elements that are the same as those of the first embodiment will be denoted by the same numerals, detailed descriptions of such elements will be omitted, and mainly the differences from the first embodiment will be described.

Figure 11:
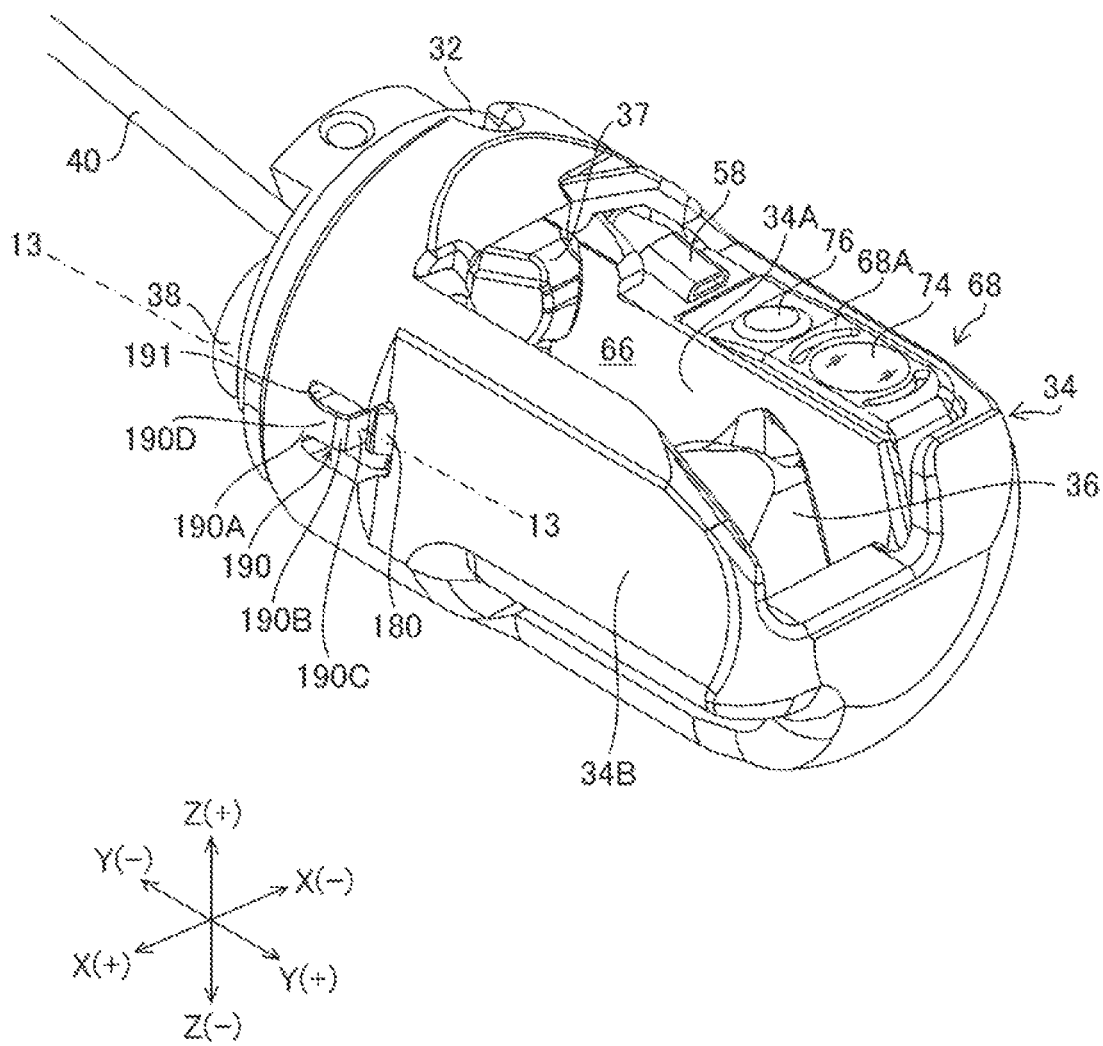
FIG. 11 is a perspective view of a distal end portion according to a second embodiment as seen from the X(+) side.
Figure 12:
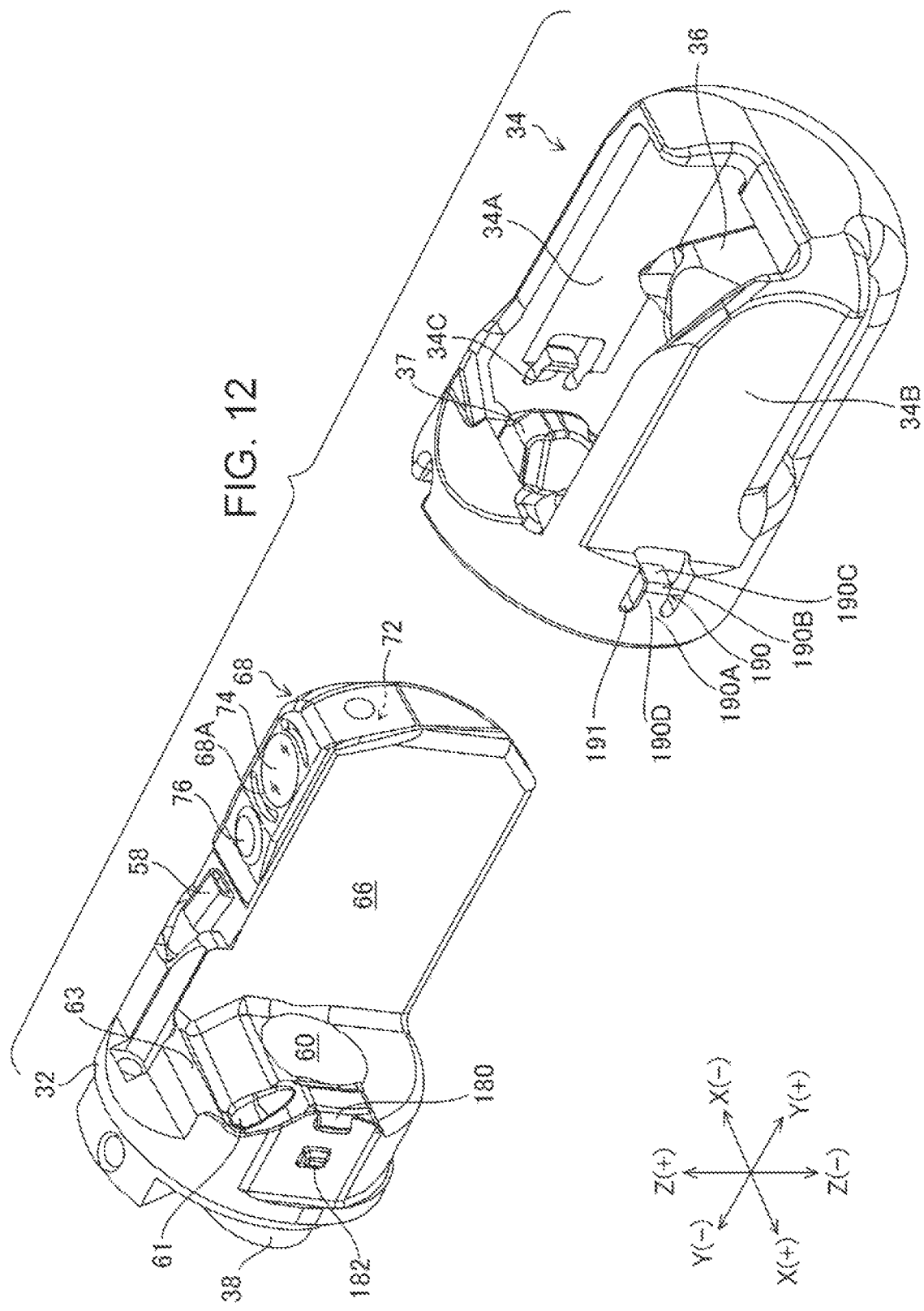
FIG. 12 is a perspective assembly view of the distal end portion illustrated in FIG. 11.
Figure 13:
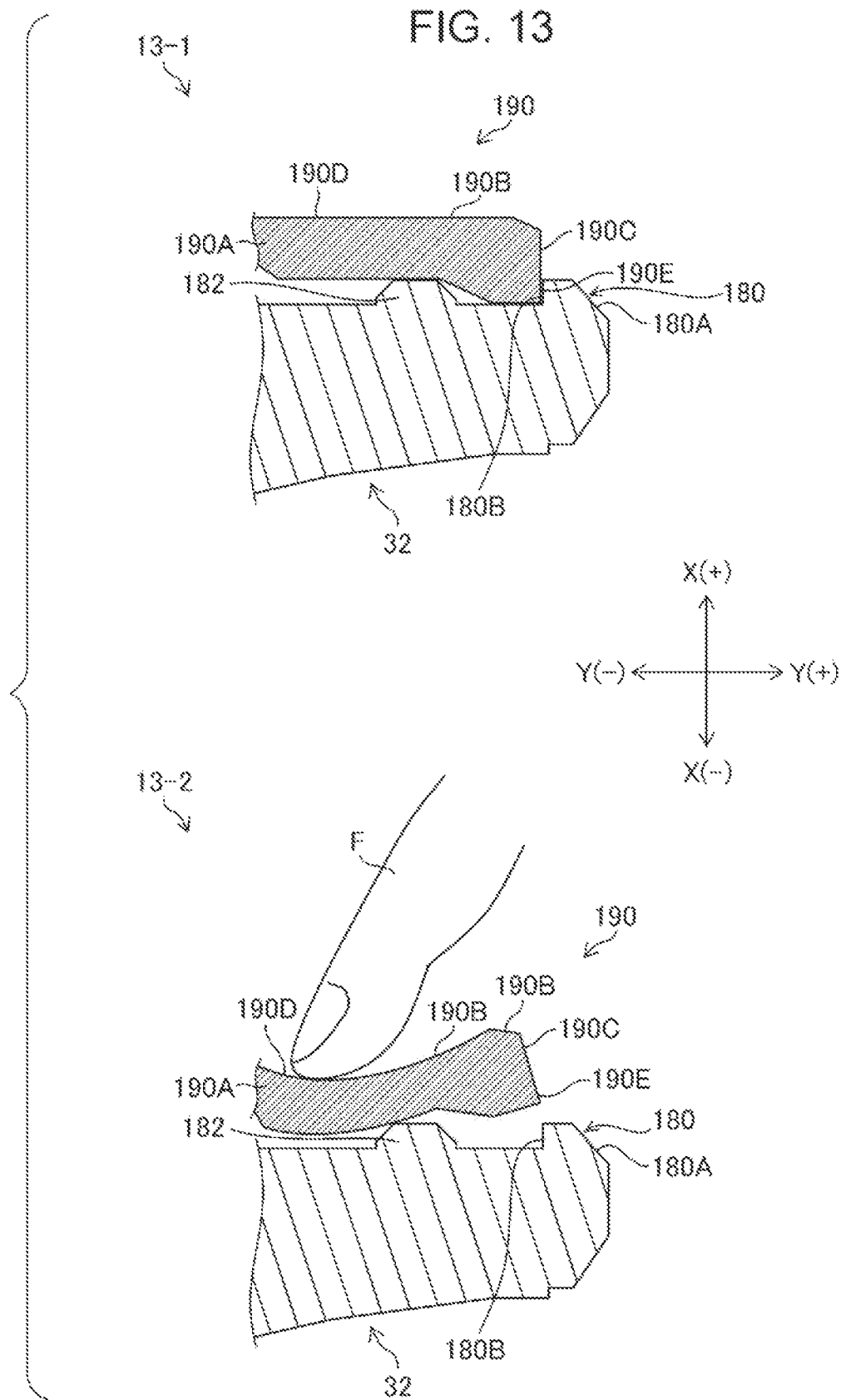
FIG. 13 illustrates an operation of attaching a cap to a distal-end-portion body and an operation of removing the cap from the distal-end-portion body according to the second embodiment.

Next, referring to FIGS. 11 to 13, an endoscope including the cap 34, which can suppress deformation due to a load and which is easily removable from the distal-end-portion body 32, will be described. FIG. 11 is a perspective view of the distal end portion 30 as seen from the X(+) side, and FIG. 12 is a perspective assembly view of the distal end portion 30. FIG. 13 illustrates operations of attaching and removing the cap. In FIG. 12, the wire 40 is not illustrated.

In the second embodiment, the shapes of a cantilever piece 190, a stopper portion 180, and a fulcrum portion 182 differ from those of the first embodiment. As illustrated in FIGS. 11 and 12, the cap 34 has the cantilever piece 190. The cantilever piece 190 is provided on one of two wall portions 34B, which are disposed in the X(+) direction and the X(−) direction, with the open window 34A therebetween. The cantilever piece 190 is formed by providing a cutout 191 in the cap 34. The cutout 191 extends through the outside and the inside of the cap 34.

The cantilever piece 190 extends in the Y-axis direction and has a fixed end 190A, which is coupled to the cap 34, and a free end 190B, which is not coupled to the cap 34. The fixed end 190A is positioned on the proximal end side (in the Y(−) direction) relative to the free end 190B. The cantilever piece 190 is made of the same material as the cap 34. Because the free end 190B is not coupled to the cap 34, the free end 190B is displaceable in the X(+) direction and the X(−) direction.

A stopper-target portion 190C is provided at the free end 190B of the cantilever piece 190. The stopper-target portion 190C engages with the stopper portion 180.

The cantilever piece 190 has a pressing portion 190D that is positioned between the fixed end 190A and the free end 190B and that is separated from the distal-end-portion body 32. When a pressing force due to a human finger (not shown) is applied to the pressing portion 190D, the pressing portion 190D becomes elastically bent toward the X(−) side.

As illustrated in FIG. 12, the distal-end-portion body 32 has the stopper portion 180 and a fulcrum portion 182 on a side facing the cantilever piece 190. The stopper portion 180 and the fulcrum portion 182 are arranged in the Y-axis direction. The stopper portion 180 is positioned on the distal end side (in the Y(+) direction) relative to the fulcrum portion 182.

Next, referring to FIG. 13, attachment and removal of the cap 34 and the distal-end-portion body 32 will be described. FIG. 13 is a sectional view taken along line 13-13 of FIG. 11.

In a state in which the cap 34 is attached to the distal-end-portion body 32, the cantilever piece 190 is not bent as illustrated in 13-1. In the embodiment, the cantilever piece 190 is substantially in contact with the fulcrum portion 182. The pressing portion 190D of the cantilever piece 190 is separated from the distal-end-portion body 32. The term "separated" means a state in which the pressing portion 190D is not in contact with the distal-end-portion body 32 in an attached state.

As illustrated in 13-1, in the state in which the cap 34 is attached to the distal-end-portion body 32, the stopper portion 180 and the stopper-target portion 190C engage with each other. The stopper portion 180 has an inclined surface 180A that tapers toward the distal end side of the distal-end-portion body 32. The stopper portion 180 has, on the proximal end side thereof (the Y(−) direction), a perpendicular surface 180B that is perpendicular to the Y-axis direction.

As illustrated in FIG. 13, the fulcrum portion 182 is disposed on the distal end side of the distal-end-portion body 32 from the position of the perpendicular surface 180B (engagement surface) of the stopper portion 180. The fixed end 190A of the cantilever piece 190 is disposed on the proximal end side of the distal-end-portion body 32 relative to the position of the fulcrum portion 182.

When the cap 34 is being attached to the distal-end-portion body 32, the cap 34 is moved in the direction from Y(+) to Y(−). The stopper-target portion 190C *comes* into contact with the inclined surface 180A of the stopper portion 180. When the cap 34 is moved further in the Y(−) direction, the stopper-target portion 190C moves along the inclined surface 180A of the stopper portion 180, and, finally, moves over the stopper portion 180.

The stopper-target portion 190C has, on the distal end side thereof, a perpendicular surface 190E perpendicular to the Y-axis direction. The perpendicular surface 180B of the stopper portion 180 and the perpendicular surface 190E of the stopper-target portion 190C face each other, and the stopper portion 180 and the stopper-target portion 190C engage with each other. Thus, when the cap 34 moves in the Y(+) direction, a large resistance force is generated as the stopper-target portion 190C moves over the stopper portion 180. Removal of the cap 34 from the distal-end-portion body 32 is suppressed.

The term "engage" means a state in which, as seen from the Y(+) direction, the stopper portion 180 is positioned on the distal end side, the stopper-target portion 190C is positioned on the proximal end side, and the stopper portion 180 and the stopper-target portion 190C partially overlap. In the partially overlapping state, the perpendicular surfaces need not face each other.

Next, as illustrated in 13-2, when a force in the X(−) direction is applied to the pressing portion 190D by a finger F, the cantilever piece 190 bends in the X(−) direction. Because the cantilever piece 190 is in contact with the fulcrum portion 182, as illustrated in 13-2, the stopper-target portion 190C, which is provided at the free end 190B, moves toward the X(+) side with the fulcrum portion 182 as a fulcrum due to "leverage". Engagement between the stopper portion 180 and the stopper-target portion 190C is released, and the stopper-target portion 190C is removed from the stopper portion 180. The cap 34 can be easily moved from the distal-end-portion body 32 in the Y(+) direction to be removed.

Third Embodiment

Referring to the drawings, an endoscope according to a third embodiment will be described. Elements that are the same as those of the first embodiment will be denoted by the same numerals, detailed descriptions of such elements will be omitted, and mainly the differences from the first embodiment will be described.

The third embodiment differs from the first embodiment in the structure of the cap 34 and in the method of disengaging the stopper-target portion 90C and the stopper portions 80.

Figure 14:
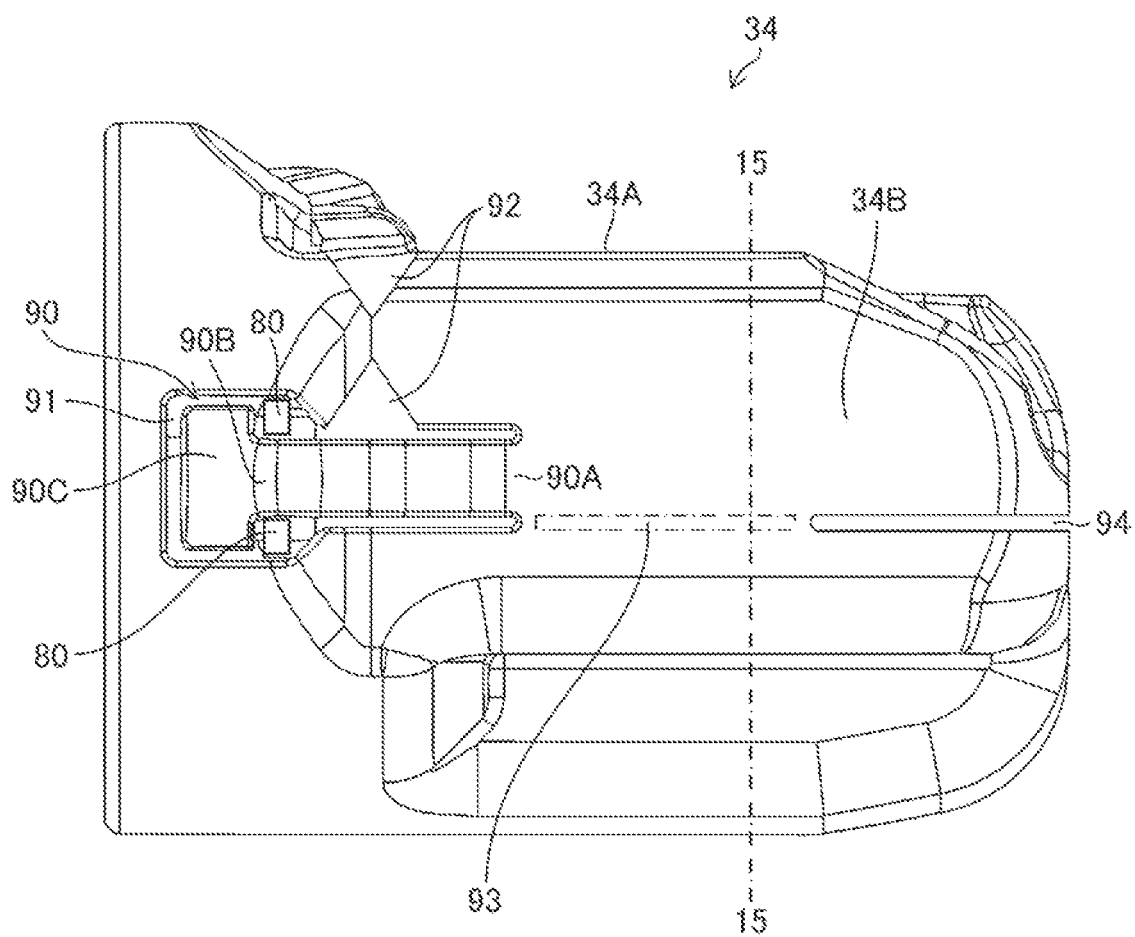
FIG. 14 is a side view of a third embodiment as seen from the X(+) side.
Figure 15:
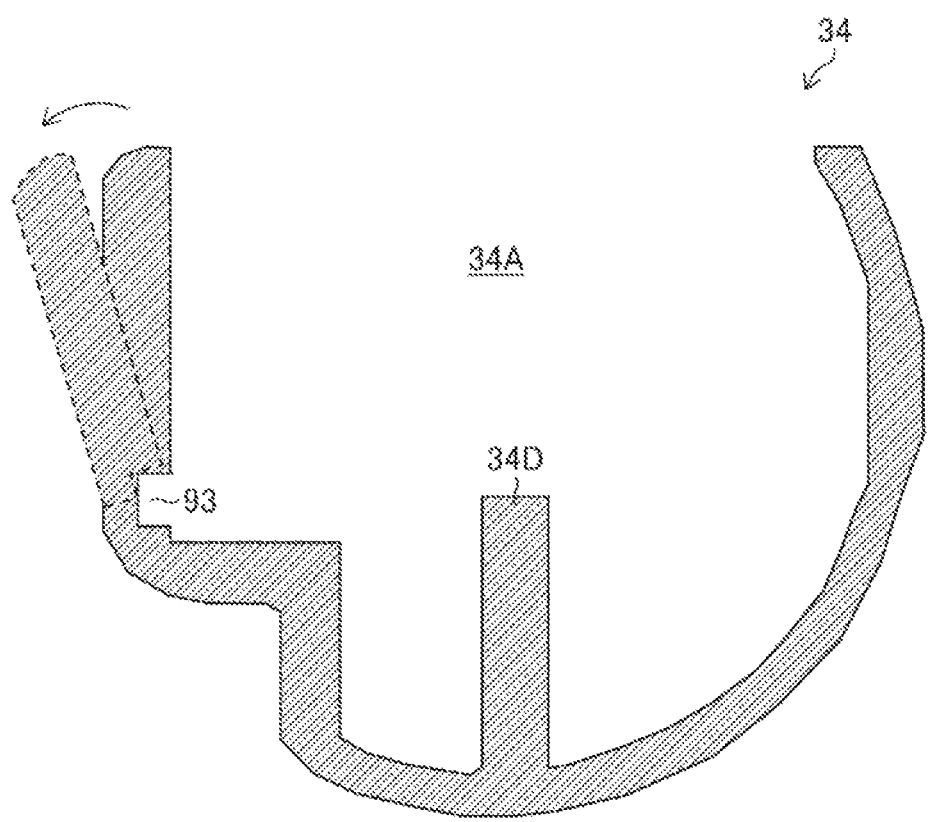
FIG. 15 is a sectional view taken along line 15-15 of FIG. 14.

FIG. 14 is a side view of the third embodiment as seen from the X(+) side. FIG. 15 is a sectional view taken along line 15-15 of FIG. 14. As illustrated in FIG. 14, the cap 34 includes the cantilever piece 90 formed by the cutout 91. The cantilever piece 90 includes the fixed end 90A, the free end 90B, and the stopper-target portion 90C provided at the free end 90B. The distal-end-portion body 32 includes the stopper portions 80. When the cap 34 is attached to the distal-end-portion body 32, the stopper portions 80 and the stopper-target portion 90C engage with each other.

Two notches 92 are formed in the cap 34. One notch 92 extends from a side of the cutout 91 in the Z(+) direction, and the other notch 92 extends from a side of the open window 34A in the Z(−) direction. The notches 92 extend through the outside and the inside of the cap 34. The Y(+) side and the Y(−) side of the cap 34 are not coupled across the notches 92. In the embodiment, one notch 92 has a shape (here, referred to as a triangular shape) that tapers in the Z(+) direction in a part thereof that is continuous with the cutout 91. The other notch 92 has a shape (here, referred to as an inverted triangular shape) that tapers in the Z(−) direction. The two notches 92 are in a positional relationship perpendicular to the cantilever piece 90. Here, "perpendicular" includes "completely perpendicular" and "substantially perpendicular". Here, "perpendicular" includes a case where the angle (smaller angle) between the cantilever piece 90 and the notches 92 is 80° or greater. The shapes of the notches 92 are not limited to the shapes illustrated in FIG. 14. In the embodiment, the cap 34 is not separated between the apex of the notch 92 having a triangular shape and the apex of the notch 92 having an inverted triangular shape. An additional notch may be formed between the vertices. The additional notch may be a continuous notch or a perforated tear-off notch. The notches 92 facilitate braking of the cap 34. In the embodiment, two notches 92 are shown. However, there may be only one notch 92. It is possible to break the cap 34, provided that there is a notch 92 that extends in the Z(−) direction from the side of the open window 34A.

The cap 34 has a small-thickness portion 93 that is parallel to the cantilever piece 90. The small-thickness portion 93 extends in the Y(+) direction from a position near the fixed end 90A of the cantilever piece 90. The small-thickness portion 93 does not reach a distal end portion of the cap 34.

As illustrated in FIG. 15, the small-thickness portion 93 has a groove portion formed inside the cap 34, and has a shape having a smaller thickness than the other portions. The term "parallel" includes "completely parallel" and "substantially parallel".

As illustrated in FIG. 14, the cap 34 includes a cutout 94 that has a linear shape and that extends from the small-thickness portion 93 in the Y(+) direction. The cutout 94 extends through the outside and inside of the cap 34. The Z(+) side and the Z(−) side of the cap 34 are not coupled across the cutout 94.

Next, a method of disengaging the stopper portions 80 and the stopper-target portion 90C will be described. As illustrated in FIG. 14, because the cap 34 has the notches 92 and the small-thickness portion 93, the rigidity of the cap 34 is reduced.

It is possible to break the cap 34 with the small-thickness portion 93 as a fulcrum by applying a force in the direction of an arrow (the X(+) direction) to the cap 34 as illustrated in FIG. 15, at a position in the Y(+) direction from the notch 92 and in the Z(+) direction from the small-thickness portion 93 (see FIG. 14). Due to breakage of the cap 34, the stopper portions 80 and the stopper-target portion 90C are disengaged, and the cap 34 is removed from the distal-end-portion body 32. It becomes easy to break the cap 34 by providing the linear cutout 94. The linear cutout 94 need not be provided. As long as the stopper portions 80 and the stopper-target portion 90C can be disengaged, breakage of the cap 34 may be deformation of the cap 34, and it is not necessary to cut and separate the cap 34 into a plurality of pieces. The cap 34 that is not separated is treated as one component and can be easily discarded.

Heretofore, the present invention has been described. The present invention is not limited to the examples described above, and may be improved or modified within the spirit and scope of the present invention. The present invention is applicable to an endoscope including an elevator in a distal-end-portion body, an endoscope in which an elevator wire is coupled to a lever of a distal-end-portion body, and the like.

REFERENCE SIGNS LIST 10 endoscope
12 endoscope system
14 processor device
16 light source device 18 display
20 elevating operation lever
22 operation section
24 insertion section
26 flexible portion
28 bending portion
30 distal end portion
32 distal-end-portion body
34 cap
34A open window
34B wall portion
34C cap-side latch portion
34D bearing
36 elevator
36A treatment-tool guiding surface
36B rotation shaft
37 contact member
38 treatment tool channel
40 elevating operation wire
42 air/water supply tube
46 operation section body
48 grip portion
50 breakage preventing tube
52 universal cable
54 light source connector
56 electric connector
57 air/water supply button
58 air/water supply nozzle
59 suction button
60 treatment-tool lead-out port
61 through-hole
62 angle knob
63 stopper portion
64 treatment-tool insertion port
66 elevator housing space
68 partition wall
68A upper surface
72 optical-system housing chamber
74 illumination window
76 observation window
78 body-side latch portion
80 stopper portion
80A inclined surface
80B perpendicular surface
82 fulcrum portion
84 groove portion
90 cantilever piece
90A fixed end
90B free end
90C stopper-target portion
90D pressing portion
90E perpendicular surface
91 cutout
93 small-thickness portion
94 cutout
100 treatment tool
102 guidewire
180 stopper portion
180A inclined surface
180B perpendicular surface
182 fulcrum portion
190 cantilever piece
190A fixed end
190B free end
190C stopper-target portion
190D pressing portion
190E perpendicular surface
191 cutout
Ax longitudinal-axis direction
F finger

What is claimed is:

1. An endoscope comprising:
   an operation section in which an operation member is provided;
   an insertion section that is provided on a distal end side of the operation section and that is to be inserted into a subject;
   a distal-end-portion body that is positioned at a distal end of the insertion section and that has a treatment-tool lead-out port;
   an elevator that is disposed on the distal end side of the treatment-tool lead-out port and that is rotatable between a lowered position and an elevated position around a rotation shaft that is perpendicular to a longitudinal-axis direction of the insertion section; and
   a cap that is removably attached to the distal-end-portion body and that has a wall portion that defines an open window in a direction perpendicular to both the longitudinal-axis direction of the insertion section and to the rotation shaft,
   wherein the cap, that is to be inserted into the subject, includes a cantilever piece that is formed on the wall portion on at least one of sides facing each other with the open window therebetween and is configured to elastically bend, the cantilever piece having a fixed end and a free end, and the cantilever piece including a stopper-target portion that is provided at the free end,
   wherein the distal-end-portion body includes a stopper portion on a side facing the cantilever piece, the stopper portion being configured to engage with the stopper-target portion, and
   wherein the stopper-target portion is removable from the stopper portion.

2. The endoscope according to claim 1,
   wherein the cantilever piece includes a pressing portion that is positioned between the fixed end and the free end and that is separated from the distal-end-portion body,
   wherein the distal-end-portion body has a fulcrum portion at a position facing a part of the cantilever piece between the pressing portion and the free end, and
   wherein, by pressing the pressing portion toward the distal-end-portion body, the cantilever piece is bent with the fulcrum portion as a fulcrum to release engagement between the stopper portion and the stopper-target portion.

3. The endoscope according to claim 2, wherein the fulcrum portion is disposed on the distal end side of the distal-end-portion body from a position of the stopper portion, and the fixed end of the cantilever piece is disposed on the distal end side of the distal-end-portion body relative to a position of the fulcrum portion.

4. The endoscope according to claim 2,
   wherein the fulcrum portion is disposed at a position on a proximal end side of the distal-end-portion body relative to a position of the stopper portion, and
   wherein the fixed end of the cantilever piece is disposed on the proximal end side of the distal-end-portion body relative to the position of the fulcrum portion.

5. The endoscope according to claim 3,
   wherein the stopper-target portion has a width greater than a width of any other part of the cantilever piece, and
   wherein the stopper portion is narrower than the stopper-target portion, and the stopper portion is formed of a member that defines a groove portion that is wider than any other part of the cantilever piece.

6. The endoscope according to claim 1,
wherein the cap includes, in the wall portion on which the cantilever piece is formed, a notch that is perpendicular to the cantilever piece and a small-thickness portion which is parallel to the cantilever piece and in which a thickness of the wall portion is reduced, and
wherein, by deforming the cap along the small-thickness portion, the cap is broken at the notch to release engagement between the stopper portion and the stopper-target portion.

7. The endoscope according to claim 1, wherein the stopper portion has an inclined surface that spreads outward from the distal end side toward a proximal end side of the distal-end-portion body.

8. The endoscope according to claim 1, wherein a contact member is provided at a position facing a treatment-tool guiding surface of the elevator when the elevator is in the elevated position.

9. The endoscope according to claim 8, wherein the cap and the contact member are formed of an integrally molded body.

10. The endoscope according to claim 1, wherein the elevator is attached to the cap so as to be rotatable around the rotation shaft.

* * * * *